United States Patent
Noda et al.

(10) Patent No.: US 6,550,309 B1
(45) Date of Patent: Apr. 22, 2003

(54) GAS SENSOR WITH MULTIPLE MECHANICAL AND THERMAL SHOCK CUSHION LAYERS

(75) Inventors: Keiichi Noda, Ichinomiya (JP); Kazuo Taguchi, Nagoya (JP); Hisaharu Nishio, Tokai (JP); Katsuhisa Yabuta, Komaki (JP); Koji Kano, Saitama (JP); Koichi Shimamura, Tokyo (JP); Mitsuo Kusa, Saitama (JP)

(73) Assignee: NGK Spark Plug Co., Ltd. (JP)

( * ) Notice: Subject to any disclaimer, the term of this patent is extended or adjusted under 35 U.S.C. 154(b) by 0 days.

(21) Appl. No.: 09/219,823

(22) Filed: Dec. 23, 1998

(30) Foreign Application Priority Data

Dec. 26, 1997 (JP) .............................. 9-367546
Dec. 17, 1998 (JP) ......................... 10-358481

(51) Int. Cl.$^7$ ............................. G02N 27/04
(52) U.S. Cl. ...................... 73/31.05; 73/23.2; 73/23.31; 204/424
(58) Field of Search ............................ 73/23.2, 866.5, 73/23.31, 24.06, 25.05, 31.05, 31.06, 23.32; 204/424, 426; 338/273, 233, 274, 317, 34

(56) References Cited

U.S. PATENT DOCUMENTS

| | | | |
|---|---|---|---|
| 3,772,177 A | * 11/1973 | Rittiger et al. | 204/422 |
| 3,920,172 A | 11/1975 | Rhee | |
| 4,040,930 A | 8/1977 | Dillon | |
| 4,310,401 A | * 1/1982 | Stahl | 204/428 |
| 4,818,363 A | * 4/1989 | Bayha et al. | 204/426 |
| 4,958,514 A | * 9/1990 | Takami et al. | 422/98 |

(List continued on next page.)

FOREIGN PATENT DOCUMENTS

| | | |
|---|---|---|
| EP | 0 704 697 A1 | 4/1996 |
| JP | 60-211345 | 10/1985 |
| JP | 02-001540 | 1/1990 |
| JP | 6-23964 | 6/1994 |
| JP | 9-257745 A | 10/1997 |
| JP | 10-253578 | 9/1998 |

OTHER PUBLICATIONS

Translation of portions of Japanese Utility Model No. 6-23964.

Primary Examiner—Hezron Williams
Assistant Examiner—Michael Cygan
(74) Attorney, Agent, or Firm—Brinks Hofer Gilson & Lione

(57) ABSTRACT

A gas sensor 1 includes an outer cylinder 18, a metallic shell 3, and a sensor element 2. The metallic shell 3 is disposed inside the outer cylinder 18. The sensor element 2 is disposed in a through-hole 30 formed in the metallic shell 3 and is adapted to detect a component of a gas to be measured. A sealing material layer 32 is mainly made of glass and is disposed between the inner surface of the metallic shell 3 and the outer surface of the sensor element 2. A cushion layer 34 formed of a porous inorganic substance is disposed in contact with the end of the sealing material layer 32 on the front-end side with respect to the axial direction of the sensor element 2. A cushion layer 33 formed of talc glass is disposed in contact with the end of the sealing material layer 32 on the rear-end side with respect to the axial direction of the sensor element 2. A gas sensor according to the present invention is especially adapted for use in a motorcycle and includes a sensor element having lower susceptibility to mechanical shock or thermal stress induced by different rates of contraction between a sealing material layer and an adjacent component element as well as excellent durability.

2 Claims, 5 Drawing Sheets

U.S. PATENT DOCUMENTS

| | | | |
|---|---|---|---|
| 5,037,526 A | * 8/1991 | Kato et al. | 204/428 |
| 5,202,154 A | * 4/1993 | Matsuura et al. | 427/125 |
| 5,238,551 A | * 8/1993 | Katsu et al. | 204/426 |
| 5,302,274 A | * 4/1994 | Tomantschger et al. | 204/412 |
| 5,329,806 A | * 7/1994 | McClanahan et al. | 73/31.05 |
| 5,395,641 A | * 3/1995 | Shibata et al. | 427/8 |
| 5,443,711 A | * 8/1995 | Kojima et al. | 204/426 |
| 5,467,636 A | * 11/1995 | Thompson et al. | 73/23.31 |
| 5,616,825 A | * 4/1997 | Achey et al. | 73/23.31 |
| 5,739,414 A | * 4/1998 | Paulus et al. | 73/23.31 |
| 5,846,391 A | * 12/1998 | Friese et al. | 204/424 |
| 5,886,248 A | * 3/1999 | Paulus et al. | 73/23.31 |
| 6,083,371 A | * 7/2000 | Weyl et al. | 204/426 |

* cited by examiner (a)

(b)

GAS SENSOR WITH MULTIPLE MECHANICAL AND THERMAL SHOCK CUSHION LAYERS

BACKGROUND OF THE INVENTION

1. Field of the Invention

The present invention relates to a gas sensor, such as an oxygen sensor, an HC sensor, or an $NO_x$ sensor, for detecting a component of an exhaust gas emitted from, especially, a motorcycle.

2. Description of Related Art

Conventionally, there has been known a gas sensor composed of an outer cylinder, a metallic shell disposed inside the outer cylinder, and a sensor element disposed inside the metallic shell for detecting a component of a measurement gas. In a gas sensor having such a structure, a gap between the outer surface of the sensor element and the inner surface of the metallic shell is generally filled with a sealing material layer, as of glass.

For example, an oxygen sensor for automobile use is often mounted in an exhaust manifold or an exhaust pipe located near a suspension system and tires. In this case, a stone flipped from a tire may hit the sensor so that a mechanical shock acts on the sensor, or the sensor may be subjected to a strong thermal shock caused by splashing of water during exposure to high temperature. Further, the sensor element of the sensor has a coefficient of thermal expansion smaller than that of the sealing material layer. Therefore, in a glass sealing step, the sensor element receives a radial compressive force due to a thermal history (heating/cooling), so that stress concentration occurs in a boundary region between a portion of the sensor element covered with the sealing material layer and an uncovered portion. If a mechanical shock caused by a flipped stone or the like or a thermal shock caused by splashing of water acts on the sensor in such a state, a resultant stress acts at a boundary region (hereinafter referred to as "sealing boundary portion") between the portion of the sensor element covered with the sealing material layer and the uncovered portion, so that the sensor element is easily broken. Especially, an oxygen sensor used in a motorcycle is placed in an environment in which the oxygen sensor is likely to receive such shocks.

SUMMARY OF THE INVENTION

An object of the present invention is to provide a gas sensor in which stress caused by application of a mechanical or thermal shock on the sensor does not concentrate at the sealing boundary portion and which therefore has excellent durability.

To achieve the above object, a gas sensor of the present invention comprises an outer cylinder, a metallic shell, a sensor element, a sealing material layer, and two cushion layers. The metallic shell is joined to the outer cylinder. The sensor element is disposed inside the metallic shell and is adapted to detect a component of a measurement gas. The sealing material layer is mainly made of glass and is disposed between the inner surface of the metallic shell and the outer surface of the sensor element. The first cushion layer is disposed in contact with the end surface of the sealing material layer located on a front-end side with respect to the axial direction of the sensor element. The first cushion layer is formed of a mixture containing filler particles which are superior in heat resistance to glass contained in the sealing material layer, and binder particles which are superior in heat resistance to glass contained in the sealing material layer and are lower in softening temperature than the filler particles. The second cushion layer is disposed in contact with the end surface of the sealing material layer located on a rear-end side with respect to the axial direction of the sensor element. The second cushion layer is formed of a porous material containing glass whose softening temperature is slightly lower than that of the glass contained in the sealing material layer.

The above-described structure of the gas sensor of the present invention prevents local application of a strong bending stress onto the sealing boundary portion, which would otherwise occur when mechanical or thermal shock acts on the sensor element.

In general, the above-described effect of mitigating stress concentration can be achieved even when the cushion layer is disposed on only one side of the sealing material layer. However, in the case of application to a motorcycle, a gas sensor is used in an environment in which a strong mechanical or thermal shock may act on the sensor. Therefore, if the cushion layer is disposed on only one side of the sealing material layer, the sensor does not meet the shock resistance required for application to motorcycles. When the cushion layer is disposed on both sides of the sealing material layer, the sensor can sufficiently meet the shock resistance required for application to motorcycles.

DESCRIPTION OF THE PREFERRED EMBODIMENTS

Figure 1:
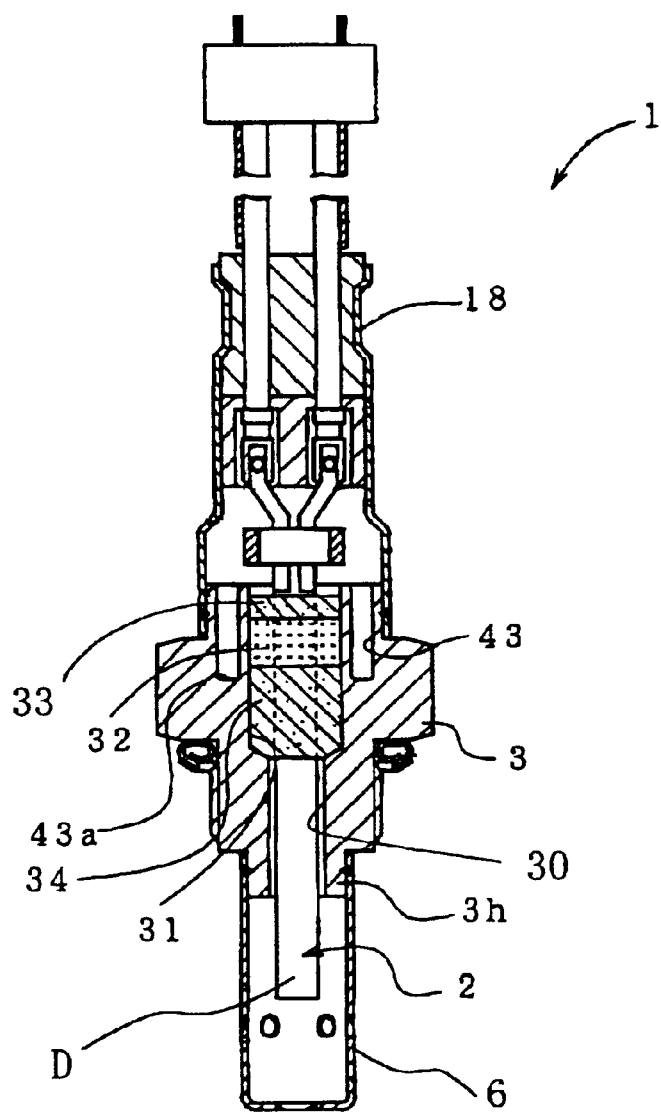
FIG. 1(a) is a longitudinal, sectional view showing an embodiment of an oxygen sensor of the present invention.
FIG. 1(b) is a view of a planar section taken through the glass seal of the embodiment shown in FIG. 1(a)
Figure 1:
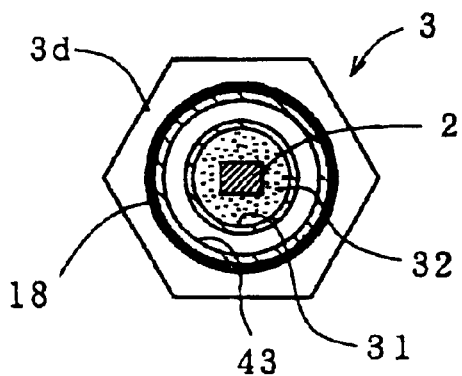

As shown in FIG. 1, the sensor element 2 has an elongated shape with a sensing portion D formed at a tip end thereof and is inserted through the metallic shell 3 such that the sensing portion D projects therefrom. In this case, the cushion layer 34 which is in contact with the front end of the sealing material layer 32 (hereinafter referred to as the "front cushion layer") contains filler particles which are superior in heat resistance to glass contained in the sealing material layer 32, as well as binder particles which partially fill gaps among filler particles, are superior in heat resistance to glass contained in the sealing material layer 32, and are lower in softening temperature than the filler particles.

Specifically, the front cushion layer 34 is more susceptible to high temperature than is the sealing material layer 32. Therefore, in the front cushion layer 34, the filler particles, which are superior in heat resistance to glass contained in the sealing material layer 32, are bonded by the binder particles, which are lower in softening temperature than the filler particles but are superior in heat resistance to glass contained in the sealing material layer. Accordingly, sufficient heat resistance is attained. In this case, the filler particles may be formed mainly of $Al_2O_3$ or talc, and are preferably formed mainly of $Al_2O_3$ in view of its excellent heat resistance. The binder particles are preferably of clay, for example, since clay particles can fuse together at a temperature of forming the sealing material layer 32 (a sealing temperature).

For the cushion layer 33 which is in contact with the rear end of the sealing material layer 32 (hereinafter referred to as the "rear cushion layer"), the requirement in relation to heat resistance is less stringent than that for the front cushion layer 34. Therefore, the rear cushion layer 33 does not have to be formed of a material having a high heat resistance, such as a material containing $Al_2O_3$ as a main component, and may be formed of talc or the like. Further in place of clay particles, glass having a softening temperature lower than that of glass used in the sealing material layer 32 may be used as a binder. The se of such glass enables stable formation of the rear cushion layer 33, while avoiding a possibility that the sealing material layer 32 re-melts due to heat treatment for fusing the rear cushion layer 33.

In the gas sensor 1 of the present invention, an annular groove 43 that surrounds the sealing material layer 32 is formed in the metallic shell 3 by cutting out a portion of the metallic shell 3. The annular groove 43 is located between the inner surface of the outer cylinder and the surface of the cavity 31 of the metallic shell 3.

In the above configuration, when the sensor 1 is in a heated state and water is splashed thereon, thus causing an abrupt temperature variation, the annular groove 43 serves as a heat-insulating layer. Also, when the sensor is subjected to a mechanical impulsive force caused by impinging foreign matter such as a pebble, a portion of the outer cylinder or a portion of the metallic shell which serves as an outer wall portion defining the annular groove 43 acts as a cushion for absorbing the mechanical impulsive force. Therefore, the annular groove 43 mitigates the thermal or mechanical shock acting on the sealing material layer 32, so that the effect of the present invention can be enhanced.

As noted, FIG. 1 shows an embodiment of a gas sensor of the present invention. An oxygen sensor 1 is adapted to detect the concentration of oxygen contained in an exhaust gas emitted from a motorcycle. The oxygen sensor 1 includes an elongated ceramic element 2 (sensor element). The tip of the ceramic element 2 is exposed to high-temperature exhaust gas flowing through an exhaust pipe.

Figure 2:
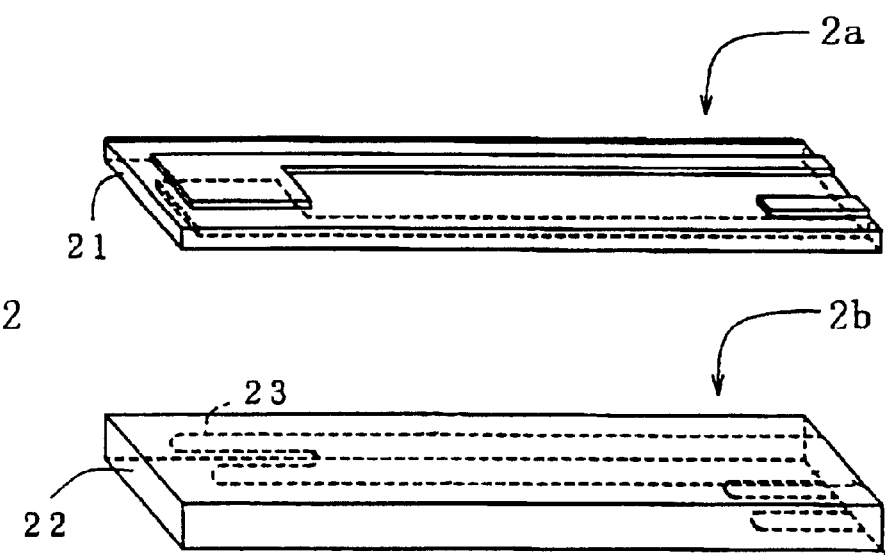
FIG. 2 is an explanatory view showing the structure of a ceramic element serving as a sensor element of the sensor of FIG. 1.

The ceramic element 2 is an elongated sheet having a rectangular section. As shown in FIG. 2, the ceramic element 2 is a laminate of an oxygen concentration cell element 2a and a heater 2b. The oxygen concentration cell element 2a has an elongated sheet form. The heater 2b also has an elongated sheet form and is adapted to heat the oxygen concentration cell element 2a to a predetermined activation temperature. The oxygen concentration cell element 2a is made of an oxygen-ion conductive solid electrolyte 21. A typical example of such a solid electrolyte 21 is $ZrO_2$ obtained through solid solution of $Y_2O_3$ or CaO. Alternatively, a solid solution of $ZrO_2$ and an oxide of an alkali earth metal or rare earth metal may be used. The heater 2b is a known ceramic heater composed of a ceramic substrate 22 and a resistance-heating pattern 23. The resistance-heating pattern 23 is made of a high-melting-point metal and is embedded in the ceramic substrate 22.

As shown in FIG. 1, the ceramic element 2 having the above structure is inserted through a through-hole 30 of the metallic shell 3 and is fixed to the metallic shell 3. A cavity 31 communicates with the rear end of the through-hole 30, and the other end of the cavity 31 opens at the rear end surface of the metallic shell 3. The cavity 31 has a diameter larger than that of the through-hole 30. A space which is defined by the outer surface of the ceramic element 2 and the inner surface of the metallic shell 3 which defines the cavity 31 is filled for sealing purpose with a sealing material layer 32. The sealing material layer 32 is mainly made of glass (for example, crystallized zinc silica boric-acid glass; softening temperature 684° C.).

Within the chamber 31, cushion layers 33 and 34 are formed on opposite sides of the sealing material layer 32. The cushion layers 33 and 34 are made of a porous inorganic substance. The porous inorganic substance for the front cushion layer 34 includes filler particles formed mainly of $Al_2O_3$, and the binder particles formed of clay.

The clay particles may be mainly composed of hydrous alumino-silicate. For example, the clay particles may be mainly composed two or more clay minerals (or their composite substances) selected from the group consisting of allophane, imogolite, hisingerite, smectites, kaolinite, halloysite, montmorillonite, illite, vermiculite, and dolomite. From the point of view of oxide components, the clay particles may contain $SiO_2$ and $Al_2O_3$ and, as needed, may further contain singly or in combination $Fe_2O_3$, $TiO_2$, CaO, MgO, $Na_2O$, and $K_2O$. For example, in the present embodiment, the clay particles contain 84% by weight $Al_2O_3$ and 10% by weight $SiO_2$ as oxides and kaolinite and dolomite in appropriate amounts.

The rear cushion layer 33 is formed of talc particles and crystallized glass having a softening temperature slightly lower than that of glass contained in the sealing-material layer 32 (e.g., crystallized zinc silica boric-acid glass; softening temperature 680° C.).

Figure 4:
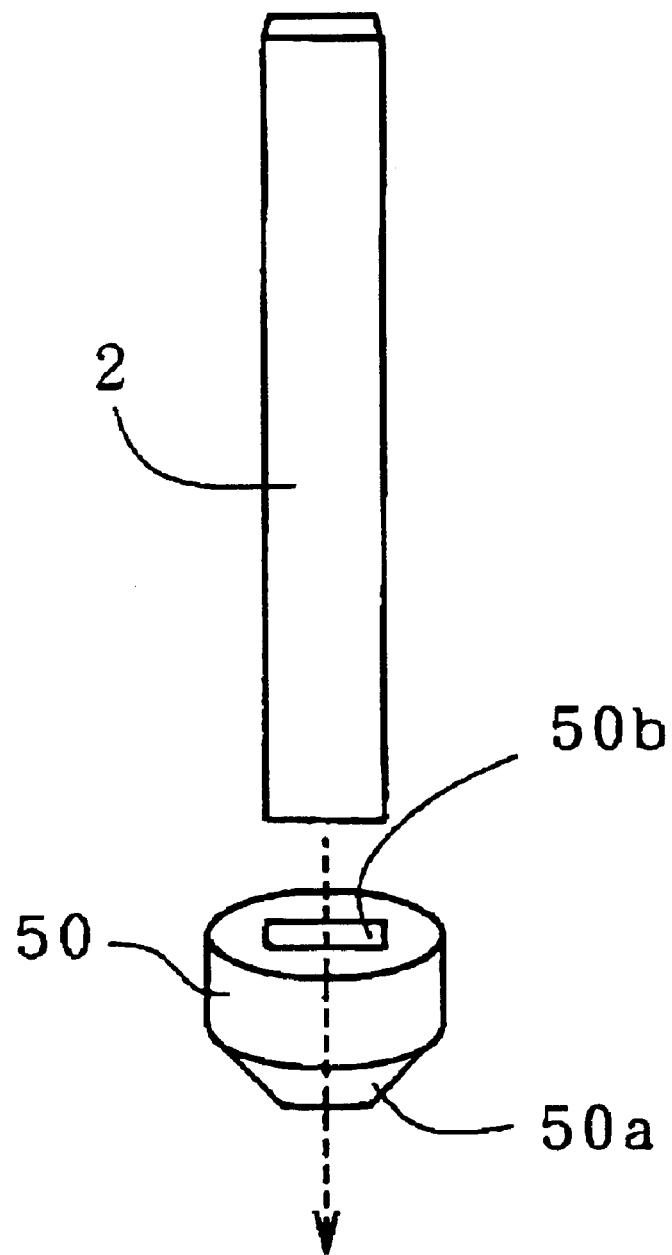
FIG. 4 is an explanatory view illustrating a process for manufacturing the oxygen sensor of FIG. 1.

The above-mentioned sealed structure of the ceramic element 2 and the metallic shell 3 is manufactured in the following manner, for example. First, a material powder compact for forming the cushion layer 34 is manufactured. In the present embodiment, $Al_2O_3$ powder serving as the filler particles and clay powder serving as the binder particles are mixed. The resulting mixture is pressed into a powder compact 50 shown in FIG. 4. The powder compact 50 has a through-hole 50b formed in a central portion thereof and in the axial direction thereof.

Next, the ceramic element 2 is inserted through the through-hole 50b formed in the powder compact 50. Then, the ceramic element 2 is inserted from its tip through the through-hole 30 formed in the metallic shell 3. The powder compact 50 is placed in the cavity 31 of the metallic shell 3 and is lightly pressed against the metallic shell 3 in the axial direction of the ceramic element 2. Next, an inorganic material powder which is mainly composed of glass is formed into a cylindrical shape, yielding a powder compact. The powder compact is fitted onto the ceramic element 2 from the rear end of the ceramic element 2 in such a manner that the ceramic element 2 is inserted through a through-hole formed in the powder compact. Thus, the powder compact is placed in the cavity 31 adjacent to the powder compact 50, thereby obtaining an insulator-sensor-element assembly.

The insulator-sensor-element assembly is heated to 850° C. As a result, the powder compact becomes the sealing material layer 32 through fusion of the inorganic material powder which is mainly composed of glass, thereby sealing the ceramic element 2 against the metallic shell 3. The powder compact 50 becomes the cushion layer 34 through fusion of the clay powder while $Al_2O_3$ particles are dispersed.

Next, a material powder (in the present embodiment, a mixed powder of talc and the above-described crystallized zinc silica boric-acid glass) for the cushion layer 33 is filled into a space between the ceramic element 2 and the metallic shell 3 at a rear portion of the cavity 31. The charged material powder is lightly pressed. Subsequently, the insulator-sensor-element assembly is again heated to 800° C. As a result, the charged material powder becomes the cushion layer 33 through fusion of the crystallized glass powder. In place of directly filling the material powder into the cavity 31, the material powder may be pressed into a compact, which is then placed in the cavity 31.

Next, a protection cover 6 is fixedly attached to the tip portion of the metallic shell 3 through laser welding or resistance welding (for example, spot welding) in such a manner as to cover a projected portion of the ceramic element 2. A rear end portion of the metallic shell 3 is fitted into a tip end portion of an outer cylinder 18. At the fitted overlap of the metallic shell 3 and the outer cylinder 18, the metallic shell 3 and the outer cylinder 18 are circumferentially welded together (for example, through laser welding). At the fitted overlap, the metallic shell 3 and the outer cylinder 18 may be connected through circumferential caulking in place of laser welding.

Figure 3:
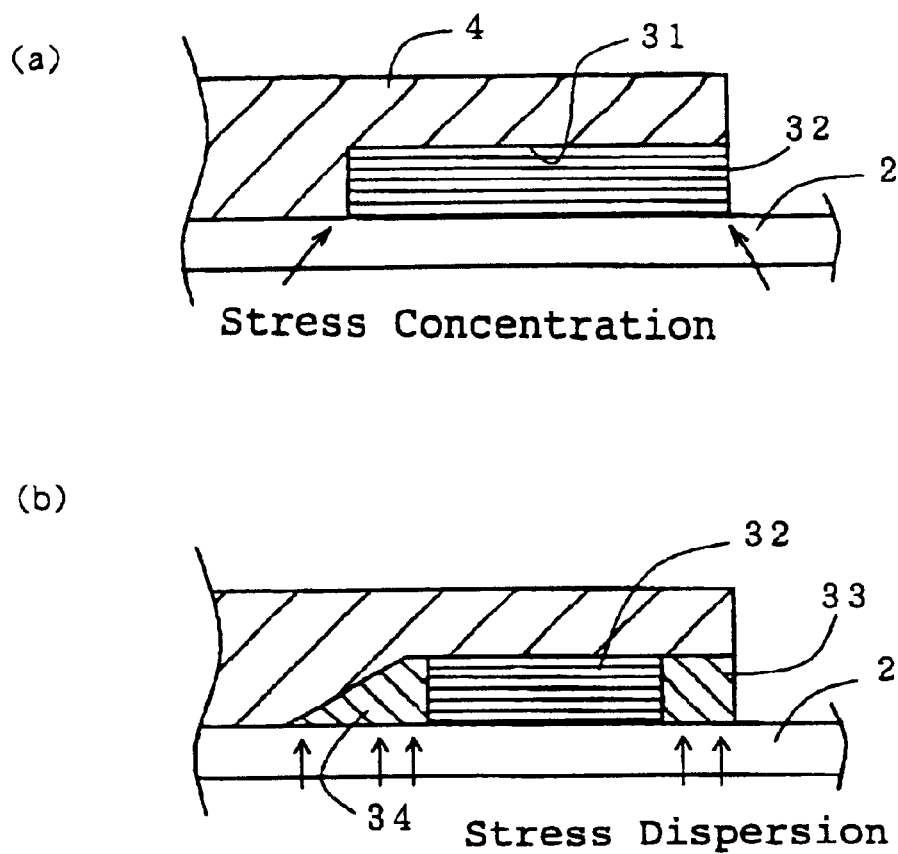
FIG. 3(a) is an explanatory view showing the point of stress concentration in prior art devices.
FIG. 3(b) is an explanatory view showing the action of a cushion layer.

The oxygen sensor 1 is often attached to an exhaust manifold or an exhaust pipe located near a suspension system and tires of a vehicle. In this case, a flipped stone or the like may hit the sensor, or the sensor may be subjected to a strong thermal shock caused by splashing of water during exposure to high temperature. According to the configuration of a conventional oxygen sensor, as shown in FIG. 3(a), the cavity 31 is merely filled with the sealing material layer 32 which is mainly composed of glass. For example, when a bending stress is applied to the ceramic element 2 due to a shock caused by a flipped stone or thermal shock, stress concentration tends to occur in a boundary region between a portion of the ceramic element 2 covered with the sealing material layer 32 and an uncovered portion in the axial direction of the ceramic element 2, causing a potential breakage of the ceramic element 2.

By contrast, according to the above-described configuration of the oxygen sensor 1 of the present invention, as shown in FIG. 3(b), the cushion layers 33 and 34 made of a porous inorganic substance are disposed on opposite sides of the sealing material layer 32 with respect to the axial direction of the ceramic element 2. Accordingly, even when the force of a mechanical or thermal shock acts on the ceramic element 2, stress concentration is less likely to occur in the above-mentioned boundary region, so that breakage of the ceramic element 2 hardly occurs. In this case, since the cushion layers 33 and 34 support the portions of the ceramic element 2 which are not covered with the sealing material layer 32, stress can be dispersed which would otherwise concentrate at the sealing boundary portion.

As shown in FIG. 1, an annular groove 43 that surrounds the sealing material layer 32 is formed in the metallic shell 3 by cutting out a portion of the metallic shell 3 and is located between the surface of the cavity 31 and the inner surface of the outer cylinder 18. A bottom 43a of the groove 43 is located beyond the sealing material layer 32 toward the tip of the ceramic element 2 with respect to the axial direction of the ceramic element 2.

Figure 5:
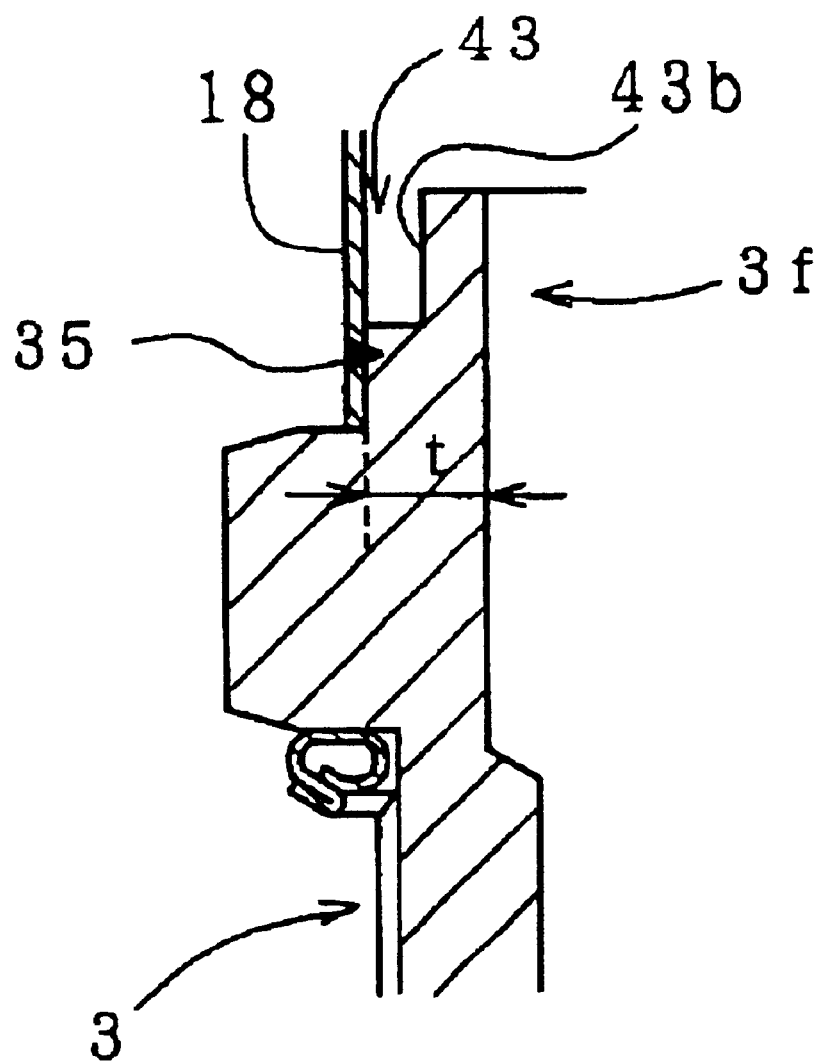
FIG. 5 is an longitudinal, sectional view showing a modification of the annular groove formed in the metallic shell.

The annular groove 43 may be formed in a matter as shown in FIG. 5. That is, the rear end portion of the metallic shell 3 is fitted into the outer cylinder 18. An annular cutout 43b is formed, and the groove 43 is defined by the outer cylinder 18 and the cutout 43b (in place of the cutout 43b, groove-shaped depressions may be formed at predetermined intervals in the circumferential direction). The metallic shell 3 and the outer cylinder 18 are connected through a welding portion 35 (or caulking portion) formed along the circumferential direction. This configuration is effective in the case where the thin-walled portion 3f of the metallic shell 3—in which the annular groove 43 is to be formed—has relatively small thickness t.

In the above embodiments, the gas sensor assumes the configuration of a $\lambda$ sensor, which employs only an oxygen concentration cell element as a sensor element (ceramic element). However, the sensor element may be of a different type, such as a full-range oxygen sensor element or an $NO_x$ sensor element.

We claim:

1. A gas sensor, comprising, in combination:

an outer housing;

a metallic shell joined to said outer housing, said metallic shell defining a through passageway having an inner surface and an annular cutout extending circumferentially about said through passageway and axially along a portion of said through passageway;

a sensor element disposed inside said through passageway of said metallic shell and adapted to detect a component of a measurement gas;

a sealing material layer mainly made of glass and disposed between said inner surface of said metallic shell adjacent said annular cutout and an outer surface of said sensor element;

a first cushion layer disposed in contact with said inner surface of said metallic shell and an end surface of said sealing material layer located on a front-end side with respect to an axial direction of said sensor element, said first cushion layer being formed of a mixture containing filler particles which are superior in heat resistance to glass contained in said sealing material layer, and binder particles which are superior in heat resistance to glass contained in said sealing material layer and are lower in softening temperature than said filler particles; and a second cushion layer disposed in contact with said inner surface of said metallic shell and an end surface of said sealing material layer located on a rear-end side with respect to the axial direction of said sensor element, said second cushion layer being formed of a mixture containing filler particles and a binder containing glass whose softening temperature is slightly lower than that of the glass contained in said sealing material layer.

2. A gas sensor according to claim 1 wherein the gas sensor is used in a motorcycle.

* * * * *